(12) United States Patent
Smith et al.

(10) Patent No.: US 8,574,167 B2
(45) Date of Patent: Nov. 5, 2013

(54) NEEDLE FOR BIOPSY DEVICE

(75) Inventors: Eric B. Smith, Cincinnati, OH (US);
Shailendra K. Parihar, Mason, OH (US); Michael J. Andreyko, Cincinnati, OH (US); Kyle P. Moore, Mason, OH (US); James Janszen, Cleves, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 539 days.

(21) Appl. No.: 12/843,092

(22) Filed: Jul. 26, 2010

(65) Prior Publication Data

US 2010/0312140 A1    Dec. 9, 2010

Related U.S. Application Data

(63) Continuation-in-part of application No. 12/335,578, filed on Dec. 16, 2008, now abandoned.

(51) Int. Cl.
*A61B 10/00*    (2006.01)

(52) U.S. Cl.
USPC ........... 600/566; 600/562; 600/563; 600/564; 600/565; 600/567

(58) Field of Classification Search
USPC ................................................. 600/562–567
See application file for complete search history.

(56) References Cited

U.S. PATENT DOCUMENTS

| | | |
|---|---|---|
| 3,561,429 A | 2/1971 | Jewett et al. |
| 4,844,088 A | 7/1989 | Kambin |
| 5,213,110 A | 5/1993 | Kedem et al. |
| 5,526,822 A | 6/1996 | Burbank et al. |
| 6,077,230 A * | 6/2000 | Gregoire et al. ............ 600/566 |
| 6,086,544 A | 7/2000 | Hibner et al. |
| 6,251,121 B1 | 6/2001 | Saadat |
| 6,626,849 B2 | 9/2003 | Huitema et al. |
| 6,976,968 B2 | 12/2005 | Ritchart et al. |
| 7,442,171 B2 | 10/2008 | Stephens et al. |
| 7,464,429 B2 | 12/2008 | Stoltz |
| 7,534,234 B2 | 5/2009 | Fojtik |

(Continued)

FOREIGN PATENT DOCUMENTS

DE    28 08 911    3/1979

OTHER PUBLICATIONS

U.S. Appl. No. 12/483,305, filed Jun. 12, 2009, Hibner et al.
U.S. Appl. No. 12/709,624, filed Feb. 22, 2010, Parihar.

(Continued)

*Primary Examiner* — Sean Dougherty
*Assistant Examiner* — Devin Henson
(74) *Attorney, Agent, or Firm* — Frost Brown Todd LLC

(57) ABSTRACT

A biopsy device comprises a body and a needle extending distally from the body. The needle comprises a cannula and a tissue piercing tip that is unitary with the cannula. The tissue piercing tip may be formed by compressing the distal end of the cannula to put two distal cannula portions in apposition with each other. One of the apposed distal cannula portions may be removed. The remaining distal cannula portion may be formed into a blade of the tissue piercing tip. A cutter may be moved relative to the needle to sever samples from tissue protruding through a transverse aperture formed in the cannula. A gap may be provided between the exterior of the cutter and the interior of the cannula, permitting the cutter to be distally vented while a proximal vacuum is communicated to the cutter to transport severed tissue samples proximally through the cutter.

16 Claims, 12 Drawing Sheets

(56) References Cited

U.S. PATENT DOCUMENTS

| | | |
|---|---|---|
| 7,645,240 B2 | 1/2010 | Thompson et al. |
| 7,806,834 B2 * | 10/2010 | Beckman et al. ............. 600/566 |
| 7,918,803 B2 | 4/2011 | Ritchart et al. |
| 2005/0065453 A1 | 3/2005 | Shabaz et al. |
| 2005/0165328 A1 | 7/2005 | Heske et al. |
| 2006/0074345 A1 | 4/2006 | Hibner |
| 2007/0032742 A1 | 2/2007 | Monson et al. |
| 2007/0149894 A1 | 6/2007 | Heske et al. |
| 2008/0004545 A1 * | 1/2008 | Garrison ....................... 600/566 |
| 2008/0027355 A1 | 1/2008 | DiCarlo |
| 2008/0214955 A1 | 9/2008 | Speeg et al. |
| 2009/0171242 A1 | 7/2009 | Hibner |
| 2009/0216152 A1 | 8/2009 | Speeg et al. |
| 2010/0152610 A1 | 6/2010 | Parihar et al. |
| 2010/0160819 A1 | 6/2010 | Parihar et al. |
| 2010/0160824 A1 | 6/2010 | Parihar et al. |

OTHER PUBLICATIONS

U.S. Appl. No. 60/869,736, filed Dec. 13, 2006, Ritchie et al.
U.S. Appl. No. 60/874,792, filed Dec. 13, 2006, Hibner et al.
International Search Report dated Mar. 4, 2010 for Application No. PCT/US2009/067120.
International Preliminary Report on Patentability and Written Opinion dated Feb. 17, 2012 for Application No. PCT/US2011/042363.
International Preliminary Report on Patentability dated Jun. 21, 2011 for Application No. PCT/US2009/067120.
Supplementary European Search Report dated Apr. 22, 2013 for Application No. EP 11814962.

* cited by examiner

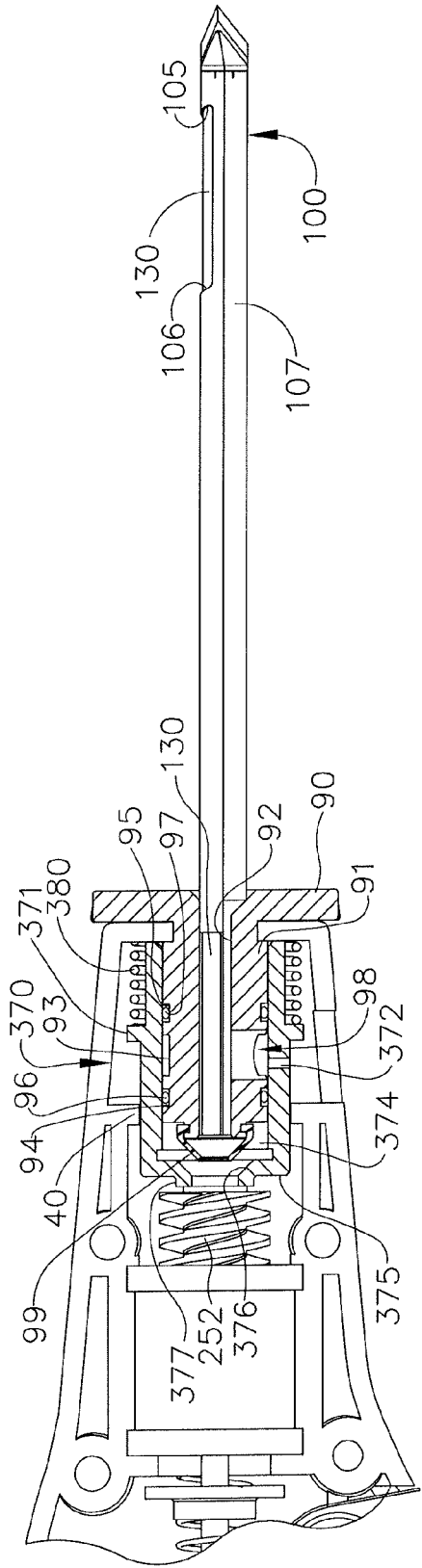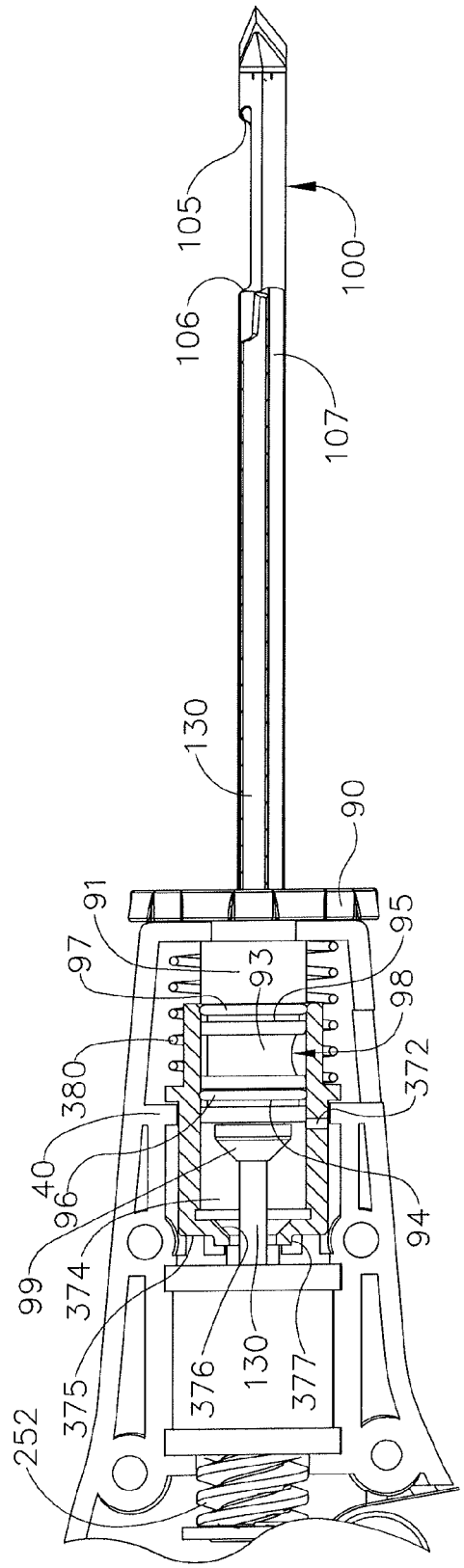

NEEDLE FOR BIOPSY DEVICE

PRIORITY

This application is a continuation-in-part of U.S. patent application Ser. No. 12/335,578, entitled "Hand Actuated Tetherless Biopsy Device with Pistol Grip," filed Dec. 16, 2008, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. An exemplary biopsy device is the MAMMOTOME® brand device from Ethicon Endo-Surgery, Inc. of Cincinnati, Ohio. Biopsy devices may be used under stereotactic guidance, ultrasound guidance, MRI guidance, or otherwise.

Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Non-Provisional patent application Ser. No. 12/335,578, entitled "Hand Actuated Tetherless Biopsy Device with Pistol Grip," filed Dec. 16, 2008; U.S. Non-Provisional patent application Ser. No. 12/337,942, entitled "Biopsy Device with Central Thumbwheel," filed Dec. 18, 2008; and U.S. Non-Provisional patent application Ser. No. 12/483,305, entitled "Tetherless Biopsy Device with Reusable Portion," filed Jun. 12, 2009. The disclosure of each of the above-cited U.S. patents, U.S. patent Application Publications, and U.S. patent Applications is incorporated by reference herein.

While several systems and methods have been made and used for obtaining a biopsy sample, it is believed that no one prior to the inventors has made or used the invention described in the appended claims.

BRIEF DESCRIPTION OF THE FIGURES

While the specification concludes with claims which particularly point out and distinctly claim the biopsy device, it is believed the present biopsy device will be better understood from the following description of certain examples taken in conjunction with the accompanying drawings, in which like reference numerals identify the same elements and in which:

FIG. 11 is a side cross-sectional view of a needle portion and an auto pressure regulator of the biopsy device of FIG. 1, with the auto pressure regulator open to admit atmospheric pressure air into the needle portion;

FIG. 12 is a side cross-sectional view of the needle portion and auto pressure regulator of FIG. 11, with the auto pressure regulator moved proximally to prevent atmospheric pressure air from entering into the into the needle portion;

DETAILED DESCRIPTION

The following description of certain examples of the biopsy device should not be used to limit the scope of the present biopsy device. Other examples, features, aspects, embodiments, and advantages of the biopsy device will become apparent to those skilled in the art from the following description, which is by way of illustration, one of the best modes contemplated for carrying out the biopsy device. As will be realized, the biopsy device is capable of other different and obvious aspects, all without departing from the spirit of the biopsy device. Accordingly, the drawings and descriptions should be regarded as illustrative in nature and not restrictive.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 1:
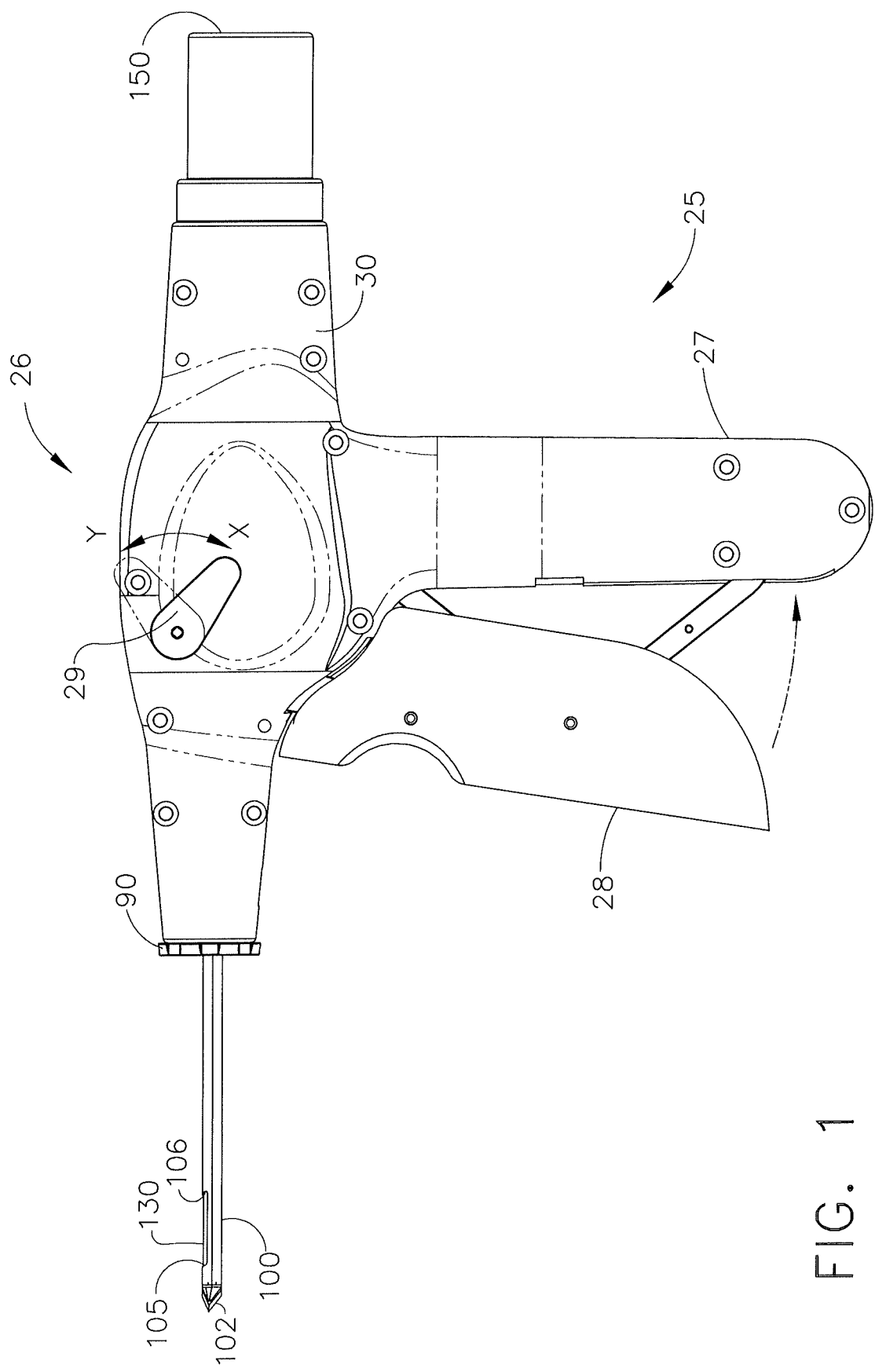
FIG. 1 is a left side view of an exemplary biopsy device.

FIG. 1 shows an exemplary biopsy device (25) that is small enough to be hand held, is entirely self contained, and can collect one or more biopsy tissue samples from a patient. Biopsy device (25) comprises an exemplary tissue cutting mechanism (200) (FIGS. 2-4) and an exemplary vacuum generating mechanism (300) (FIGS. 5-6) that are powered by one or more movements of an operator's hand to capture, cut, transport, and collect tissue samples from a patient, such as from a patient's breast.

Figure 2:
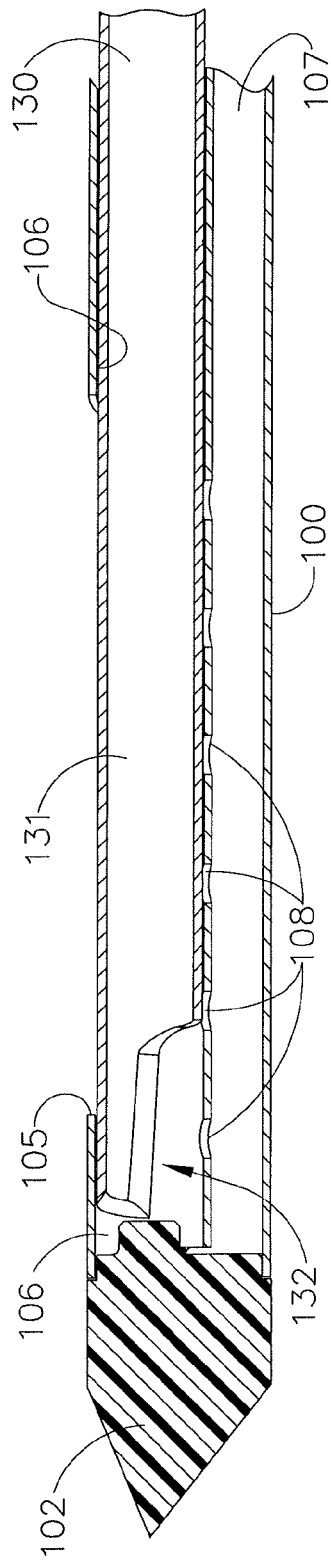
FIG. 2 is a side cross sectional view of a needle portion of the biopsy device of FIG. 1.

Hand powered biopsy device (25) of the present example comprises a body (26) with a pistol grip (27), and a manually actuatable trigger (28). A rotatable needle portion (100) defines a longitudinal axis of biopsy device (25) and extends distally from body (26). As shown in FIG. 2, needle portion (100) comprises a distal tissue piercing tip (102) and a hollow cutter passage (106) extending proximally therefrom into body (26). A tissue receiving aperture (105) is located proximal from piercing tip (102) and opens into hollow cutter passage (106) for tissue capture therein. A hollow cutter (130) of the tissue cutting mechanism (200) is slidably and rotatably positioned within cutter passage (106) to cut tissue drawn into aperture (105). Cutter (130) extends through biopsy device (25), from needle portion (100) and through body (26), to operably connect with a tissue collection chamber (150) removably attached to a proximal end of body (26). Tissue samples can be cut with cutter (130) and then drawn through hollow cutter (130) and into tissue collection chamber (150) with vacuum mechanism (300) as will be described in greater detail below. A directional reversal lever (29) is located on each side of biopsy device (25) to reverse directional movement of cutter (130) as tissue samples are acquired. As shown, directional reversal lever (29) has a first downward position X and a second upward position Y.

I. Exemplary Needle Portion

FIG. 2 shows a cross sectional view of the exemplary rotatable needle portion (100) of biopsy device (25), showing distal tissue piercing tip (102) and hollow cutter passage (106), in which cutter (130) is slidably disposed. The exemplary rotatable needle portion (100) rotatably attaches to body (26) and is rotatable about its longitudinal axis, relative to body (26). Hollow cutter (130) is shown slidably and rotatably mounted in hollow cutter passage (106), with a distal cutting end (132) adjacent to distal tissue piercing tip (102). A lateral vacuum passage (107) extends longitudinally in parallel with hollow cutter passage (106) and operably connects with hollow cutter passage (106) via a plurality of vacuum passages (108) extending therebetween. Vacuum passages (108) are provided to assist in drawing tissue into tissue aperture (105) and into hollow cutter passage (106) when hollow cutter (130) is retracted proximally, and when vacuum is applied to lateral passage (107). It should be understood, however, that these features of needle portion (100) are merely exemplary, and that needle portion (100) may be modified in any suitable fashion.

Figure 3:
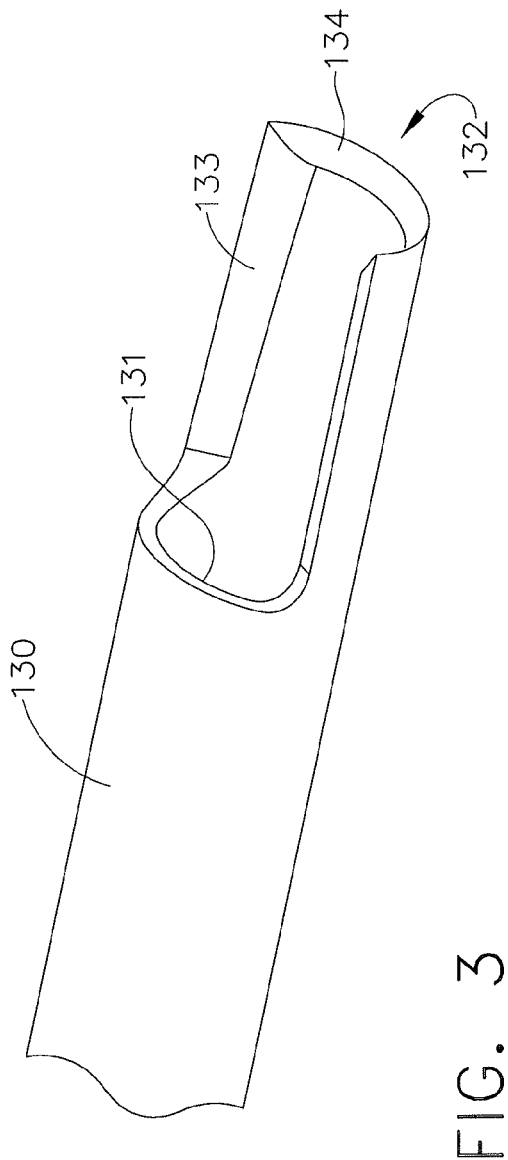
FIG. 3 is a perspective view of the distal end of a cutter of the needle portion of FIG. 2.

A perspective view of a scoop shaped distal cutting end (132) of hollow cutter (130) is shown in FIG. 3. Scoop shaped distal cutting end (132) comprises a side cutting edge (133) and a distal cutting edge (134) to cut tissue. The cutting angle for cutting edges (133, 134) may be specified as per material properties and rotation speed of cutter (130), as know through available databases or standards. Alternatively, the cutting angle for cutting edges (133, 134) may be specified based on any other factors or in any other suitable fashion. A lumen (131) extends longitudinally through hollow cutter (130). In operation, hollow cutter (130) rotates and translates to sever a tissue sample with distal cutting edge (134) cutting tissue with translational motion and side cutting edge (133) cutting tissue with rotational motion. The cut or severed tissue sample is captured within lumen (131) adjacent to cutting end (132), and may be communicated proximally through lumen (131) to reach tissue collection chamber (150). Of course, alternative versions of cutter (130) may have a variety of alternative features and configurations, if desired.

Figure 4:
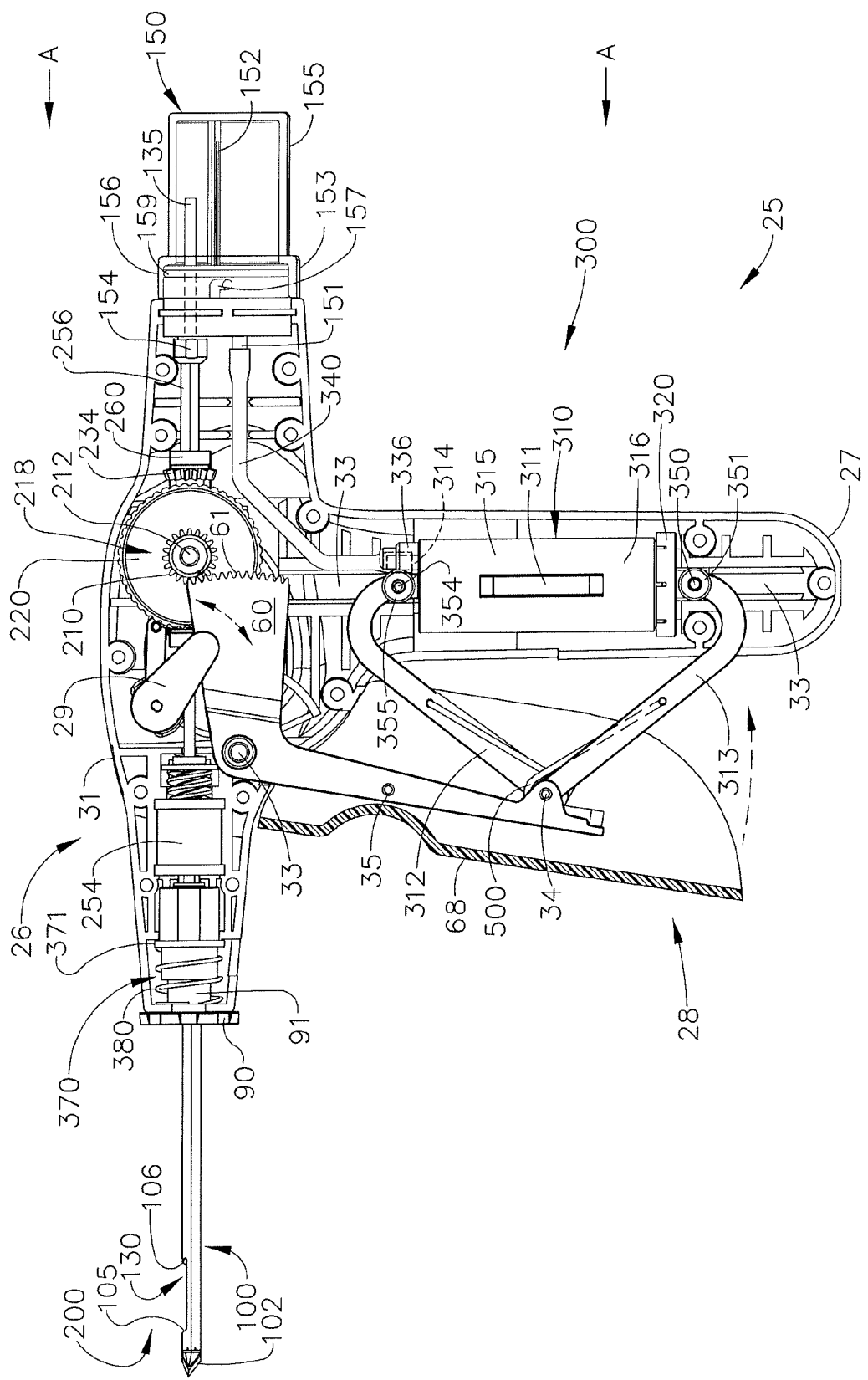
FIG. 4 is a left side view of the biopsy device of FIG. 1 with a left cover removed to show a tissue cutting mechanism and a vacuum generation mechanism.

As shown in FIGS. 1 and 4, a knurled knob (90) is fixedly attached to a proximal portion of needle portion (100), and is rotatably attached to body (26) so that rotation of knob (90) rotates needle portion (100) about its longitudinal axis, relative to body (26). Knob (90) has a cylindrical body member (91) extending proximally from knob (90) to a proximal end of needle portion (100). A proximal end of cylindrical body member (91) is open to expose lateral passage (107) and hollow cutter passage (106) and to allow the proximally extending cutter (130) to extend proximally therefrom. Knob (90) and rotatable needle portion (100) are prevented from longitudinal movement by rotational engagement with the covers (30, 31) of body (26). In other versions, however, needle portion (100) may be configured to translate. By way of example only, a spring-loaded, motorized, or other type of firing mechanism may be included to effect translational movement of needle portion (100) relative to body (26). It should also be understood that needle portion (100) need not necessarily be rotatable relative to body (26) in all versions.

J. Exemplary Alternative Needle Portion

Figure 13:
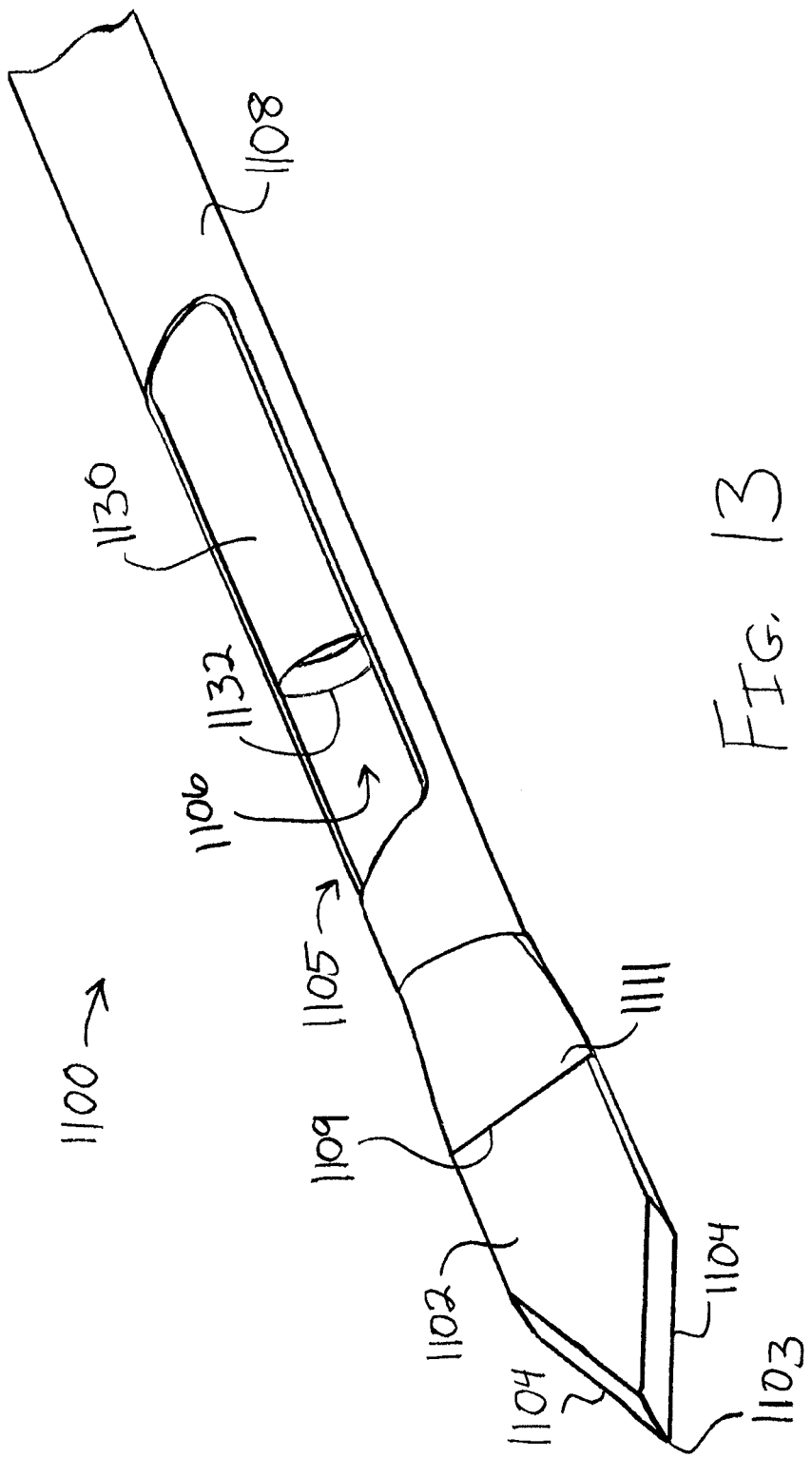
FIG. 13 is a perspective view of an exemplary alternative needle portion.
Figure 14:
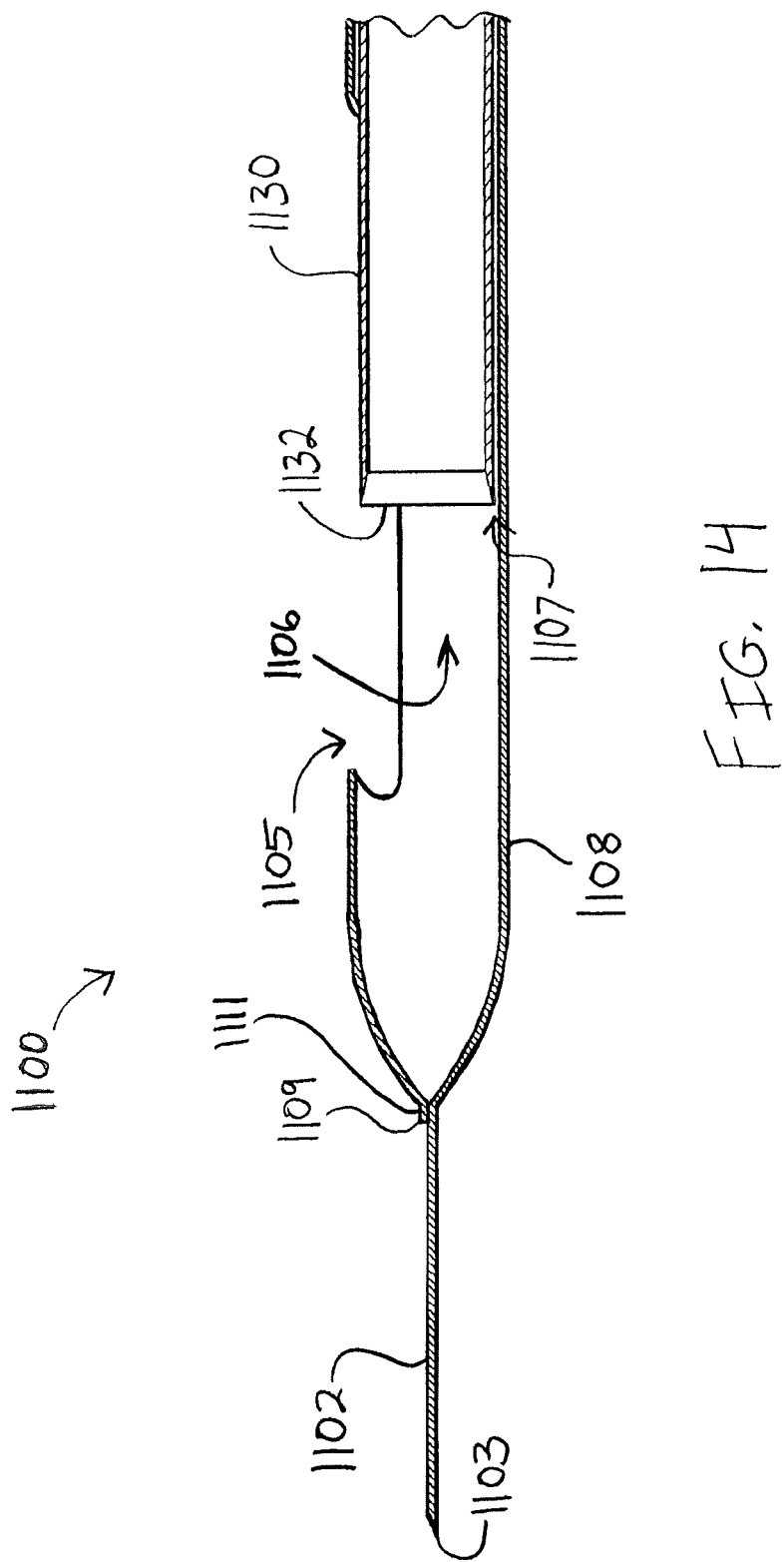
FIG. 14 is a side cross-sectional view of the needle portion of FIG. 13.

An exemplary alternative needle portion (1100) is shown in FIGS. 13-14. Needle portion (1100) of this example comprises a cannula (1108) having a transverse tissue receiving aperture (1105), an integrated distal tissue piercing tip (1102), and a hollow cutter passage (1106). Cannula (1108) may be made from stainless steel seamless drawn tubing, rolled and welded steel tubing, and/or be made from any other suitable material(s) through any other suitable process(es). While cannula (1108) of the present example has a circular cross-section, it should be understood that cannula (1108) may have any other suitable cross-section, including but not limited to oblong, ovular, elliptical, "figure eight" shaped, etc.

Figure 15:
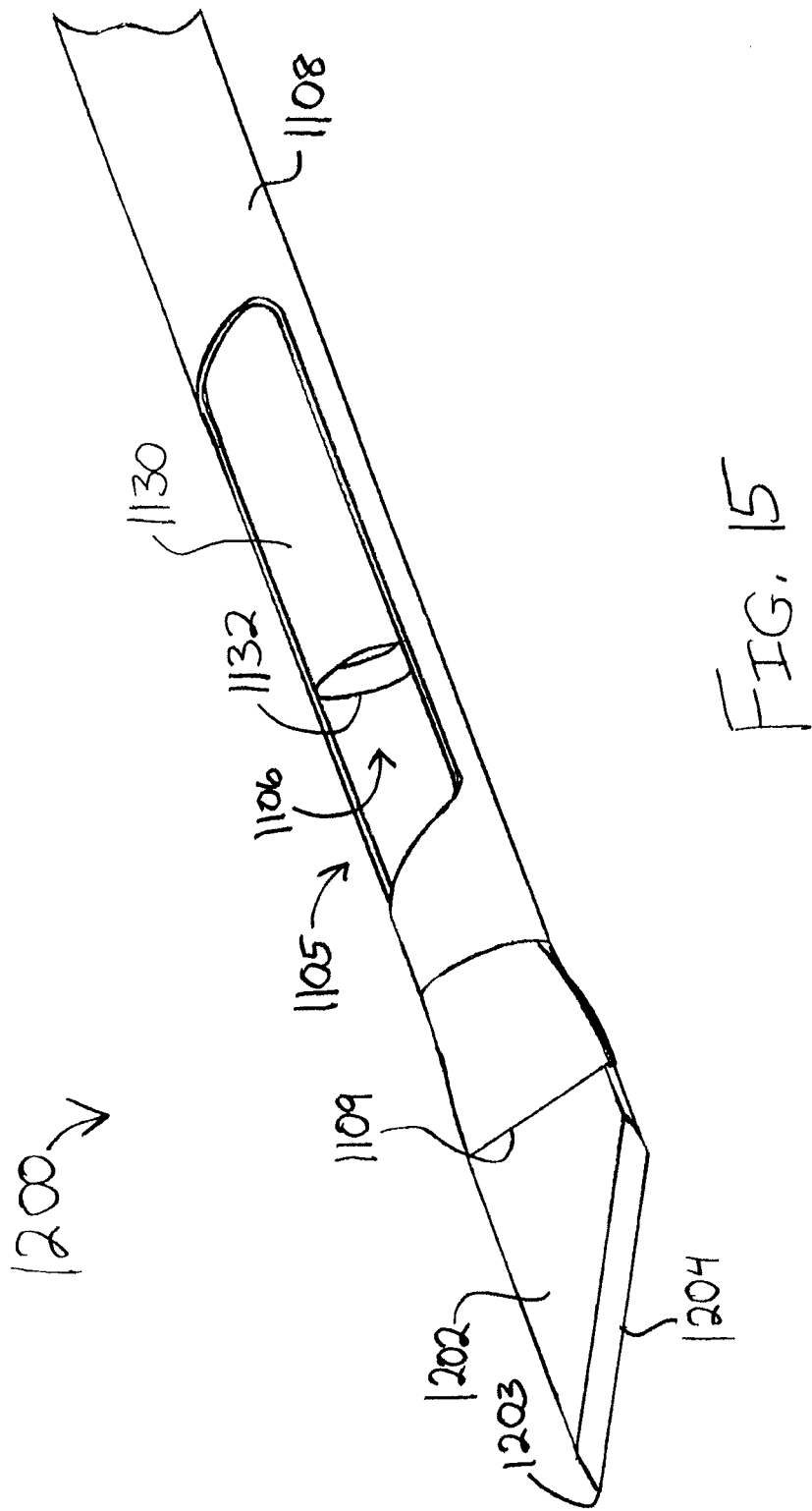
FIG. 15 is a perspective view of another exemplary alternative needle portion.

Integrated piercing tip (1102) of the present example is formed by flattening the distal end of cannula (1108) by compressing it, then grinding away the top layer of the flattened material (leaving only one wall thickness of material), and then grinding the remaining flattened material to form a blade. It should therefore be understood that integrated piercing tip (1102) and cannula (1108) are formed by a homogenous continuum of material in the present example, rather than being separately formed parts that are later joined together. In the example shown in FIGS. 13-14, the blade of integrated piercing tip (1102) is defined by two sharp edges (1104) that converge at a sharp point (1103). Of course, the blade of integrated piercing tip (1102) may alternatively take on various other shapes. By way of example only, FIG. 15 shows an exemplary alternative needle portion (1200) having an integrated piercing tip (1102) with a blade defined by a single sharp edge (1204) that terminates in a sharp point (1203). Needle portion (1200) of this example is otherwise identical to needle portion (1100). Still other various suitable forms that a blade may take will be apparent to those of ordinary skill in the art in view of the teachings herein.

In some versions where rolled and welded tubing is utilized, the weld seam may be oriented perpendicular to the flattening direction. For instance, in an example where the weld seam runs longitudinally along the length of cannula (1108), the act of compressing the distal end of cannula (1108) may be formed by moving a pressing member in a flattening direction that is transverse to the longitudinal axis of cannula (1108). In some such versions, this perpendicular orientation of the weld seam relative to the flattening direction may ensure that any cracking of the weld due to the flattening process does not appreciably affect the integrity of integrated piercing tip (1102). As can also be seen in FIGS. 13-14, the upper flattened tip layer (1111) is ground away to a point (1109) that is slightly distal to the proximal-most tangent point between the apposed top and bottom layer. This configuration may ensure little to no gap between the upper layer remnant (1111) and the remaining formed integrated piercing tip (1102), thus limiting vacuum loss in some settings. In some versions, these two apposed layers are welded, though welding is not necessary in all versions per se. In addition or in the alternative, an adhesive or filler material may be provided between the upper layer remnant (1111) and the remaining formed integrated piercing tip (1102), if desired. It should also be understood that flattened tip layer (1111) need not necessarily be ground away to point (1109) in all versions. For instance, some versions of integrated piercing tip (1102) may be formed entirely of two apposed distal layers of cannula (1108) that are ground to a blade or otherwise formed as a blade.

In some settings, forming integrated piercing tip (1102) by flattening cannula (1108) may result in the width of integrated piercing tip (1102) being wider than cannula (1108). This disparity in width may increase the dilation of tissue when needle portion (1100) is inserted into breast tissue. In some versions, the width of integrated piercing tip (1102) is greater than the circumference of cannula (1108). It should be understood that having a relatively wide piercing tip (1102) may reduce the force needed to penetrate tissue with needle portion (1100), as compared to the force that would be needed to penetrate tissue with a needle having a smaller tip width.

Needle portion (1100) of this example rotatably attaches to body (26), and is rotatable about its longitudinal axis, relative to body (26). A hollow tubular cutter (1130) is slidably disposed in hollow cutter passage (1106), and is rotatable within hollow cutter passage (1106). By way of example only, cutter (1130) may be driven by the cutter driving mechanism described above, by any of the cutter driving mechanisms described in any of the U.S. patents, U.S. patent Application Publications, and U.S. patent Applications that are referred to herein, or by any other suitable means. Cutter (1130) has a distal cutting end (1132) adjacent to integrated distal tissue piercing tip (1102). Vacuum is applied through the hollow interior of cutter (1130) in order to prolapse tissue into receiving aperture (1105). Again, vacuum may be provided by vacuum pump (310), by any vacuum source described in any of the U.S. patents, U.S. Patent Application Publications, and U.S. Patent Applications that are referred to herein, or by any other suitable means. Distal cutting end (1132) severs tissue protruding through receiving aperture (1105) as cutter (1130) is translated distally while rotating, with the severed tissue sample being captured within the hollow interior of cutter (1130).

A gap (1107) between the outer diameter of cutter (1130) and inner diameter of cannula (1108) extends longitudinally in parallel with hollow cutter passage (1106), and communicates venting to cutter (1130) in order to create a pressure differential to transport severed tissue samples proximally through cutter (1130) (e.g., to tissue collection chamber (150), etc.). In particular, gap (1107) may be vented while a vacuum is drawn through the hollow interior of cutter (1130), such that the resulting pressure differential experienced by a severed tissue sample within cutter (1130) provides proximal transport of the severed tissue sample through cutter (1130). Gap (1107) thus provides a function similar to the function provided by lateral passage (107) and vacuum passages (108) described above in the context of needle portion (100). In some versions, needle portion (1100) is provided with an internal partition, like needle portion (100), which defines a lateral passage and vacuum passages that communicate with cutter passage (1106). In other words, needle portion (100) may be provided with an integrated needle tip (1102). It should be understood that the above-described features of needle portion (1100) are merely exemplary, and that the features, configuration, and method of forming needle portion (1100) may be modified, substituted, or supplemented in any suitable fashion.

As shown, tissue piercing tip (1102) extends along a horizontal plane, with receiving aperture (1105) being positioned above the horizontal plane. In some other versions, tissue piercing tip (1102) extends along a vertical plane, with such a vertical plane passing through receiving aperture (1105). Alternatively, tissue piercing tip (1102) may extend along any other suitable plane and/or at any other suitable orientation.

While needle portion (1100) has been described in the context of biopsy device (25), it should be understood that needle portion (1100) may be readily incorporated into various other biopsy devices. By way of example only, needle portion (1100) may be readily incorporated into any of the biopsy devices taught in any of the U.S. Patents, U.S. Patent Application Publications, and U.S. Patent Applications that are referred to herein. Various suitable ways in which needle portion (1100) may be incorporated into such biopsy devices, as well as various other biopsy devices in which needle portion (1100) may be incorporated, will be apparent to those of ordinary skill in the art in view of the teachings herein.

II. Exemplary Body Portion

Figure 6:
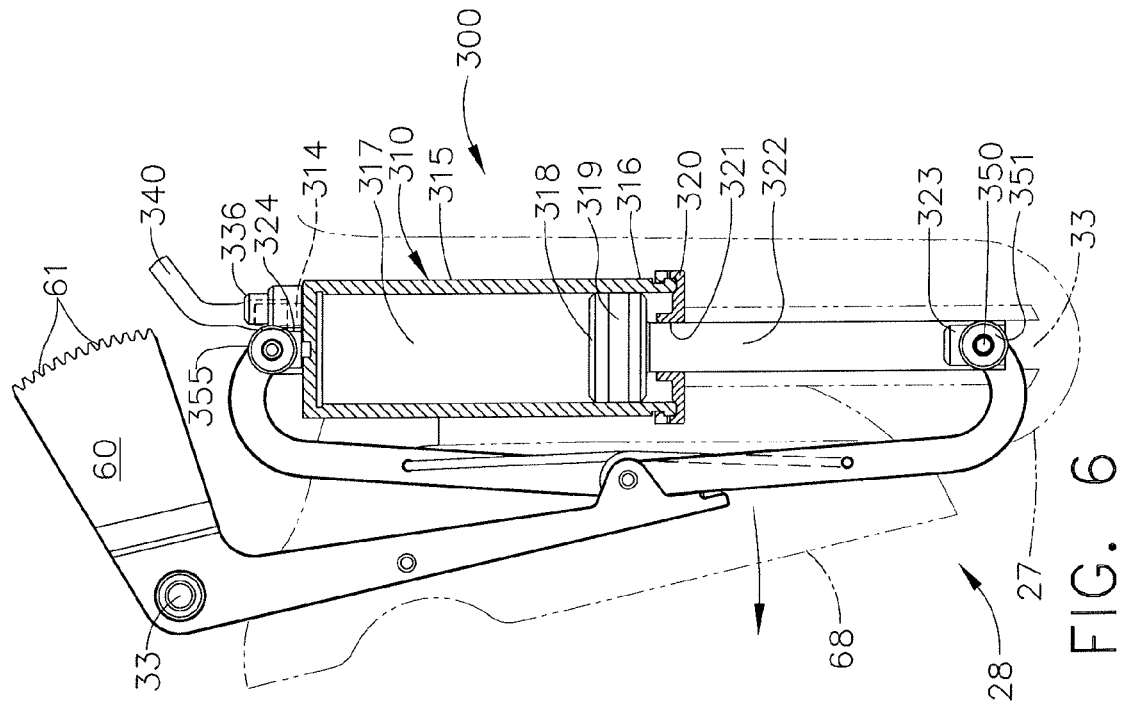
FIG. 6 is a left side view of the hand actuated vacuum pump assembly of the biopsy device of FIG. 1, in an actuated position.

FIG. 4 shows the internal elements of the biopsy device (25) of the present example with a left cover (30) removed to expose a right cover (31) of the body (26) positioned relative to other parts. Trigger (28) is pivotally attached to body (26) by a trigger pin (33) that extends from right cover (31). Trigger (28) comprises a rigid inner trigger member (60) fixedly attached to an outer trigger shell (68) by a vacuum pin (34) and a shell pin (35). Trigger shell (68) is ergonomically shaped for the operator to grasp, and is shaped to nest around pistol grip (27) when trigger (28) is moved to a fully actuated position adjacent to pistol grip (27) (FIG. 6). In FIG. 4, trigger shell (68) is sectioned vertically to show the attached inner "L" shaped inner trigger member (60). Trigger member (60) has a downward extending portion shielded by the outer trigger shell (68), and a proximally extending portion with a plurality of gear teeth (61) on a free end thereof. Gear teeth (61) are arrayed in a circular arc around trigger pin (33).

The exemplary tissue cutting mechanism (200) is engaged with trigger (28) via gear teeth (61), and the exemplary vacuum generating mechanism (300) operably engages with trigger (28) via vacuum pin (34). Manual actuation of trigger (28) from an open position (shown in FIGS. 1 and 4) to a closed position (shown in FIG. 6) against pistol grip (27)

powers both tissue cutting mechanism (200) and vacuum generation mechanism (300), as will be described in greater detail below.

A. Exemplary Hand Powered Vacuum Generation Mechanism

In the present example as shown in FIGS. 4-7, the exemplary vacuum generation mechanism (300) of hand held biopsy device (25) creates vacuum in response to one or more hand actuations of trigger (28). The vacuum created from movement of the operator's hand is used to draw tissue into tissue aperture (105) of needle portion (100), to hold the drawn tissue within needle portion (100) as a biopsy tissue sample is cut from the held tissue, and to draw the severed biopsy tissue sample through lumen (131) of cutter (130) and into tissue collection chamber (150).

1. Exemplary Vacuum Pump

As shown in FIGS. 4-7, the vacuum generation mechanism (300) comprises a hand actuated vacuum pump (310) that generates vacuum in response to an operator's manual activation of trigger (28). In the present example, vacuum pump (310) can generate 18-20 inches of mercury (inch-Hg) of vacuum (negative pressure) with one or more actuations of trigger (28). Of course, vacuum pump (310) may alternatively generate any other desired amount of pressure at any desired rate. As shown in FIG. 4, vacuum pump (310) is mounted within pistol grip (27) of body (26), and is operably connected to trigger (28) by the vacuum pin (34). Vacuum pump (310) has a pump body (315) with one or more vertical ribs (311) that slidably engage with one or more vertical grooves (33) and/or protrusions within pistol grip (27) to constrain pump (310) in the horizontal direction while allowing movement of pump (310) in the vertical direction. An upper pump arm (312) and a lower pump arm (313) comprise rigid arms that are pivotally attached to a top and a bottom (respectively) of pump body (315), and pump arms (312, 313) are pivotally connected to trigger (28) by vacuum pin (34).

Figure 5:
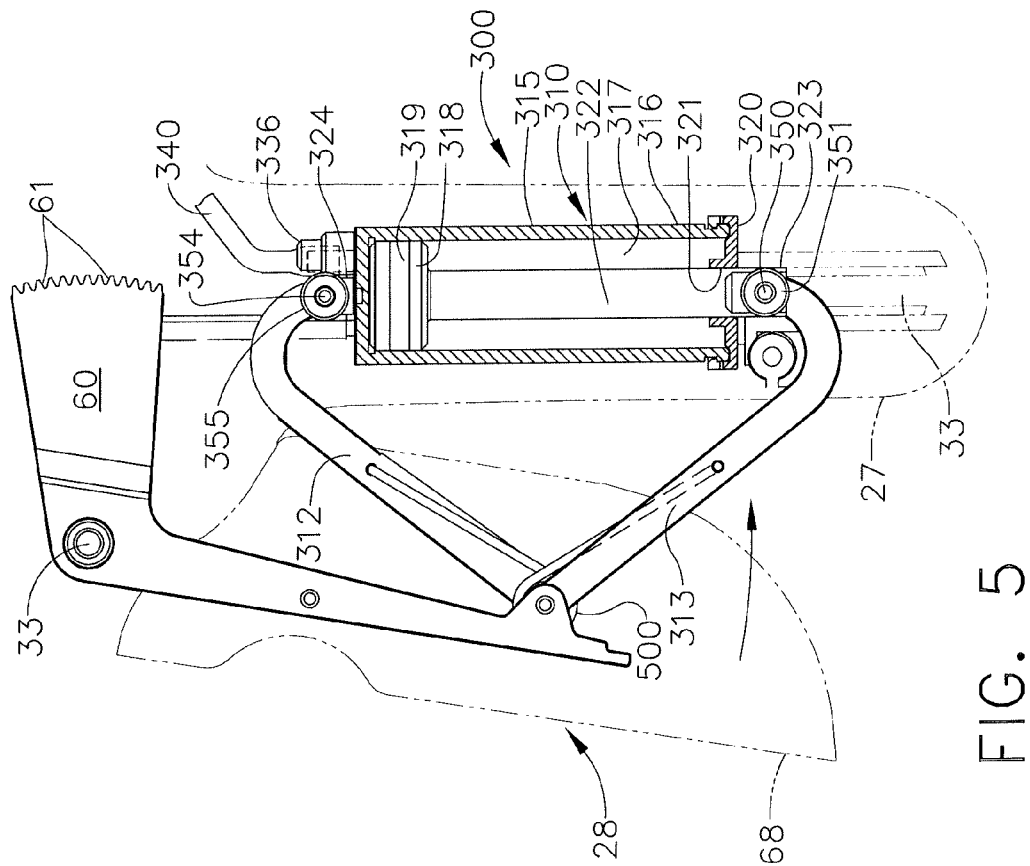
FIG. 5 is a left side view of a hand actuated vacuum pump assembly of the biopsy device of FIG. 1 in an un-actuated position.

FIGS. 5-6 show cross sectional views of pump (310), in series, as trigger (28) moves from an unactuated position (FIG. 5) to an actuated position (FIG. 6). For clarity, only vacuum pump (310) and the inner trigger member (60) are shown solid, and dashed outlines are provided to show outer trigger shell (68), pistol grip (27), and vertical groove (33) within pistol grip (27). As described previously, vacuum pump (310) is slidingly secured within pistol grip (27) by engagement of vertical ribs (311) within vertical grooves (33) of pistol grip (27), though any other suitable structures or relationships may be employed.

As shown in FIGS. 5-6, pump body (315) further comprises a cylinder portion (316) in vertical orientation, with a hollow bore (317) therein. Cylinder portion (316) has an open end and a closed end. A cylindrical piston (318) is positioned within bore (317) and is movable up and down within. A seal (319) is secured around piston (318) and forms a fixed airtight seal with the piston (318), and a sliding airtight seal with bore (317). A piston rod (322) extends downwardly from a center of piston (318) and passes through an opening (321) within a cover (320) that is fixedly attached to the open end of cylinder (316). A lower connector tang (323) extends downward from a free end of piston rod (322) and has a pin (350) extending therethrough. A proximal end of lower pump arm (313) pivotally attaches to pin (350), and rollers (351) mount on ends of pin (350) outboard of lower connector tang (323) and the proximal end of lower pump arm (313). Rollers (351) are configured to rotate within and to be guided by vertical grooves (33).

An upward connector tang (324) can be located at the top of the pump body (315) to receive pin (354). A proximal end of upper pump arm (312) piviotally attaches to pin (354), and rollers (355) mount on pin (354) outboard of upward connector tang (324) and proximal end of upper pump arm (312). Rollers (355) are configured to rotate within and to be guided by vertical grooves (33).

A spring such as a torsion spring (500) can be placed around vacuum pin (34), with a first spring arm secured to lower pump arm (313) and a second spring arm secured to upper pump arm (312). In the present example, activation of trigger (28) piviots lower pump arm (313) and upper pump arm (312) around pin (34) in a spreading motion, as shown in FIG. 6, and also spreads the first spring arm and second spring arm of torsion spring (500). When trigger (28) is released, the spread torsion spring (500) biases lower pump arm (313), upper pump arm (312), and vacuum pump (310) back to the position shown in FIG. 4.

A one way check valve or duck bill valve (336) is attached to the top of pump body (315), and is in fluid communication with bore (317). Duck bill valve (336) opens to atmosphere as piston (318) moves up to purge unwanted air from the bore (317), and closes when piston (318) moves down to draw a vacuum (negative pressure). A flexible hose (340) extends from a top of a nipple (314) and provides fluid communication from bore (317) of pump 310 to a vacuum port (151) of tissue collection chamber (150) (FIGS. 4 and 7) for the induction of a vacuum therein. Flexible hose (340) is configured to bend and move as vacuum pump (310) moves up and down when actuated and deactuated.

In FIG. 6, trigger (28) has been actuated to move cylinder (316) of pump body (315) upwardly and piston (318) and piston rod (322) downwardly to generate a vacuum therebetween. Pump body (315) is guided upwardly by the engagement of vertical ribs (311) in vertical grooves (33), and piston arm (322) is guided downwardly by clevis boss (323) within vertical grooves (33). As shown in FIGS. 5-6, and as noted above, flexible hose (340) bends as pump body (315) moves up and down in response to actuations of trigger (28).

Those of ordinary skill in the art will appreciate that vacuum generation mechanism (300) may be modified, supplemented, or substituted in a variety of ways. By way of example only, while cylinder (316) and piston (318) both move relative to body (26) when vacuum generation mechanism (300) is actuated, other versions may prevent movement of cylinder (316) or piston (318) relative to body (26) when vacuum generation mechanism (300) is actuated. As another merely exemplary alternative, a vacuum generation mechanism (300) may be actuated by something other than a trigger (28). Other suitable components, features, configurations, and methods of operating a vacuum generation mechanism (300) will be apparent to those of ordinary skill in the art in view of the teachings herein.

2. Exemplary Tissue Collection Chamber

Turning back to FIG. 4, and as noted above, tissue collection chamber (150) of the present example is operatively connected to vacuum pump (310) by flexible hose (340). Tissue collection chamber (150) is a hollow assembly that is vacuum tight and comprises a collection base (153) fixedly attached to body (26), and a tissue sample cover (155) that is removably attached to collection base (153), with a vacuum seal (159) therebetween. Collection base (153) and tissue sample cover (155) define at least one hollow volume within that can act as a vacuum accumulator for multiple actuations or pumps of vacuum pump (310). Tissue collection chamber (150) further comprises a tissue collection grid (152) extending within to receive tissue samples within. Tissue collection grid (152) may be configured to permit fluids to pass through grid (152) while preventing tissue samples from passing through grid (152). Tissue collection grid (152) may thus serve as a strainer or filter. Of course, as with other components described herein, tissue collection grid (152) may be modified, substituted, supplemented, or omitted, as desired.

Cutter (130) is operatively engaged with collection base (153) with a seal port (154) that is configured to maintain a vacuum seal with the rotatable and translatable cutter (130), even as cutter (130) rotates and translates relative to seal port (154). Vacuum generated by vacuum pump (310) is delivered to central lumen (131) of cutter (130). In other words, vacuum pump (310) may induce a vacuum within cutter lumen (131) via hose (340) and tissue collection chamber (150). Alternatively, vacuum pump (310) (or any other device) may induce a vacuum within cutter lumen (131) via any other suitable component(s) and/or route(s). In still other versions, a vacuum is simply not induced in cutter lumen (131).

Collection base (153) of the present example further comprises a proximal sample base (156) that releasably holds tissue sample cover (155) onto collection base (153). In particular, collection base (153) presents one or more outwardly extending bayonet pins that are configured to engage with one or more bayonet receivers (157) of tissue sample cover (155). Tissue sample cover (155) is released from collection base (153) by rotation of tissue sample cover (155) relative to collection base (153). Of course, tissue sample cover (155) may be selectively secured relative to body (26) using any other suitable structures, features, or techniques.

In operation, tissue cutter (130) both rotates (around the longitudinal axis) and translates (along the longitudinal axis) during the cutting and acquisition of biopsy tissue samples, and vacuum is used to draw the severed tissue from the vicinity of tissue aperture (105), through lumen (131), and into the tissue collection chamber (150). Cutter (130) has a movable proximal end (135) that is located near the top of tissue sample cover (155) to deliver tissue samples (drawn by vacuum) from proximal end (135) and onto tissue collection grid (152). Tissue collection chamber (150) is thus configured to receive and store the tissue samples on the tissue collection grid (152) as they are transferred (drawn by vacuum) from the proximal end (135) of the tissue cutter (130) and into the tissue collection chamber (150).

Those of ordinary skill in the art will appreciate that tissue collection chamber (150) may be modified, supplemented, or substituted in a variety of ways. Other suitable components, features, configurations, and methods of operating tissue collection chamber (150) will be apparent to those of ordinary skill in the art in view of the teachings herein.

3. Exemplary Auto Pressure Differentiator

As shown in FIGS. 11-12, an exemplary auto pressure regulator (370) is located at a distal end of body (26) and is configured to longitudinally slide on cylindrical body member (91) of knob (90) and to interact therewith. During manual actuation of biopsy device (25), auto pressure regulator (370) operably couples lateral passage (107) of needle portion (100) to atmospheric pressure during some portions of the tissue acquisition process, and operably decouples the lateral passageway (107) from atmospheric pressure during other portions of the tissue acquisition process. In other words, auto pressure regulator (370) of the present example is operable to selectively provide venting of lateral passage (107).

As best shown in FIGS. 11-12, cylindrical body member (91) has an inner bore (92) (with a "figure 8" type of cross section) extending longitudinally therethrough, with a proximal end of inner bore (92) forming an airtight seal with needle portion (100). Inner bore (92) is open to both lateral vacuum passage (107) and the hollow cutter passage (106) extending along needle portion (100). A frusto-conical seal (99) is located at a proximal end of open inner bore (92) and is configured to form a rotating and sliding air tight seal with cutter (130). As shown, cutter (130) extends through frusto-conical seal (99), into inner bore (92) and into hollow cutter passage (106) of needle portion (100). An exterior of cylindrical body member (91) has a proximal seal groove (94) and a distal seal groove (95) with a "U" shaped central groove (93) therebetween. Grooves (93, 94, 95) extend around cylindrical body member (91), and an open passageway (98) extends inwardly from central groove (93) to connect with open inner bore (92). An open connection exists between central groove (93), open passageway (98), inner bore (92), lateral vacuum passage (107), and hollow cutter passage (106). An o-ring or proximal elastomeric seal (96) is secured in proximal seal groove (94); and a distal elastomeric seal (97) is secured in distal seal groove (95).

Auto pressure regulator (370) further comprises a cylinder that has an inner bore (374) configured to slidingly receive cylindrical body member (91) within. Inner bore (374) is open at a distal end and has a wall (375) at a proximal end, with a tapered bore (376) extending through wall (375), and a boss (377) for passage of tissue cutter (130) therethrough. Elastomeric seals (96, 97) of cylindrical body member (91) slidingly engage with inner bore (374) to form substantially airtight seals therewith, and to seal or isolate portions of cylindrical body member (91) and central groove (93) therebetween. A centrally located air passage (372) extends through auto pressure regulator (370) and connects with inner bore (374). Auto pressure regulator (370) also has a central flange (371) that engages with a compressible spring (380) to normally bias flange (371) proximally against a rib (40) of body (26) (FIG. 12).

As shown in FIG. 12, when auto pressure regulator (370) is biased proximally against rib (40), cylindrical body member (91) is located in a distal portion of inner bore (374), with distal elastomeric seal (97) just inside the open distal end of inner bore (374) and with proximal elastomeric seal (96) distal to the centrally located air passage (372). In this biased position, open passageway (98) of the cylindrical body member (91) is sealed between seals (96, 97) and inner bore (374) (proximal to cylindrical body member (91)) is communicating with atmospheric air (e.g., vented) through air passage (372) and tapered bore (376).

In FIG. 11, tissue cutting mechanism (200) has been actuated to advance cutter (130) distally. An externally threaded screw (252) is attached around cutter (130) and has advanced distally to contact boss (377) and to push auto pressure regulator (370) distally to the position of FIG. 11. In this position, air passage (372) communicating with inner bore (374) has moved distally past proximal elastomeric seal (96) of cylindrical body member (91) and now communicates air at atmospheric pressure to central groove (93), open passageway (98), inner bore (92), and lateral vacuum passage (107). Lateral vacuum passage (107) is thus vented in this configuration and creates a pressure differential across severed tissue with vacuum induced in lumen (131) of cutter (130). This connection of air at atmospheric pressure to lateral vacuum passage (107) will be discussed further below.

Of course, auto pressure regulator (370) described herein is but one example of many possible structures or features of biopsy device (25). It will be appreciated by those of ordinary skill in the art in view of the teachings herein that the components, features, configurations, and methods of operation of auto pressure regulator (370) may be varied in numerous ways. Furthermore, auto pressure regulator (370) may be omitted altogether in some versions of biopsy device (25).

B. Exemplary Hand Powered Tissue Cutting Mechanism

As previously described, tissue cutting mechanism (200) comprises a hollow cutter (130) that is slidably and rotatably powered by one or more movements of trigger (28) by an operator's hand. Hollow cutter (130) extends longitudinally throughout biopsy device (25), from piercing tip (102) (FIG. 2) to tissue sample container (155), and rotates and translates in response to manual actuations of the trigger (28). The rotational and translational movement of hollow cutter (130) is used to sever tissue samples. The direction of rotation and the direction of translation of the cutter (130) are operator selectable with the previously mentioned directional reversal lever (29).

Tissue cutting mechanism (200) of the present example is shown in FIGS. 4 and 7-10. Directional reversal lever (29) is in the first position "X" (or downward position) as shown in FIGS. 1, 4, 7, and 9. When directional reversal lever (29) is in the first position X and trigger (28) is actuated, tissue cutting mechanism (200) translates the cutter (130) proximally along the longitudinal axis to open tissue aperture (105) and rotates the cutter (130) in a non-cutting counter clockwise direction around the longitudinal axis. A second position "Y" (or upwards position) of directional reversal lever (29) is shown as dashed lines in FIG. 1 and as solid lines in FIG. 10. When trigger (28) is actuated with directional reversal lever (29) in the second position, the directions of cutter (130) translation and rotation are reversed so that cutter (130) translates distally along the longitudinal axis to close tissue aperture (105) and to sever tissue; and rotates in a tissue cutting clockwise direction. All indicated clockwise and counterclockwise rotations of cutter (130) are described as if the observer is viewing biopsy device (25) in the direction as indicated by arrows A-A. Of course, the rotational directions described herein could be reversed if desired. Furthermore, in some versions, cutter (130) may simply not rotate at all. For instance, a non-rotating cutter (130) may lack the scoop-like distal end configuration that is shown in the present example.

Figure 9:
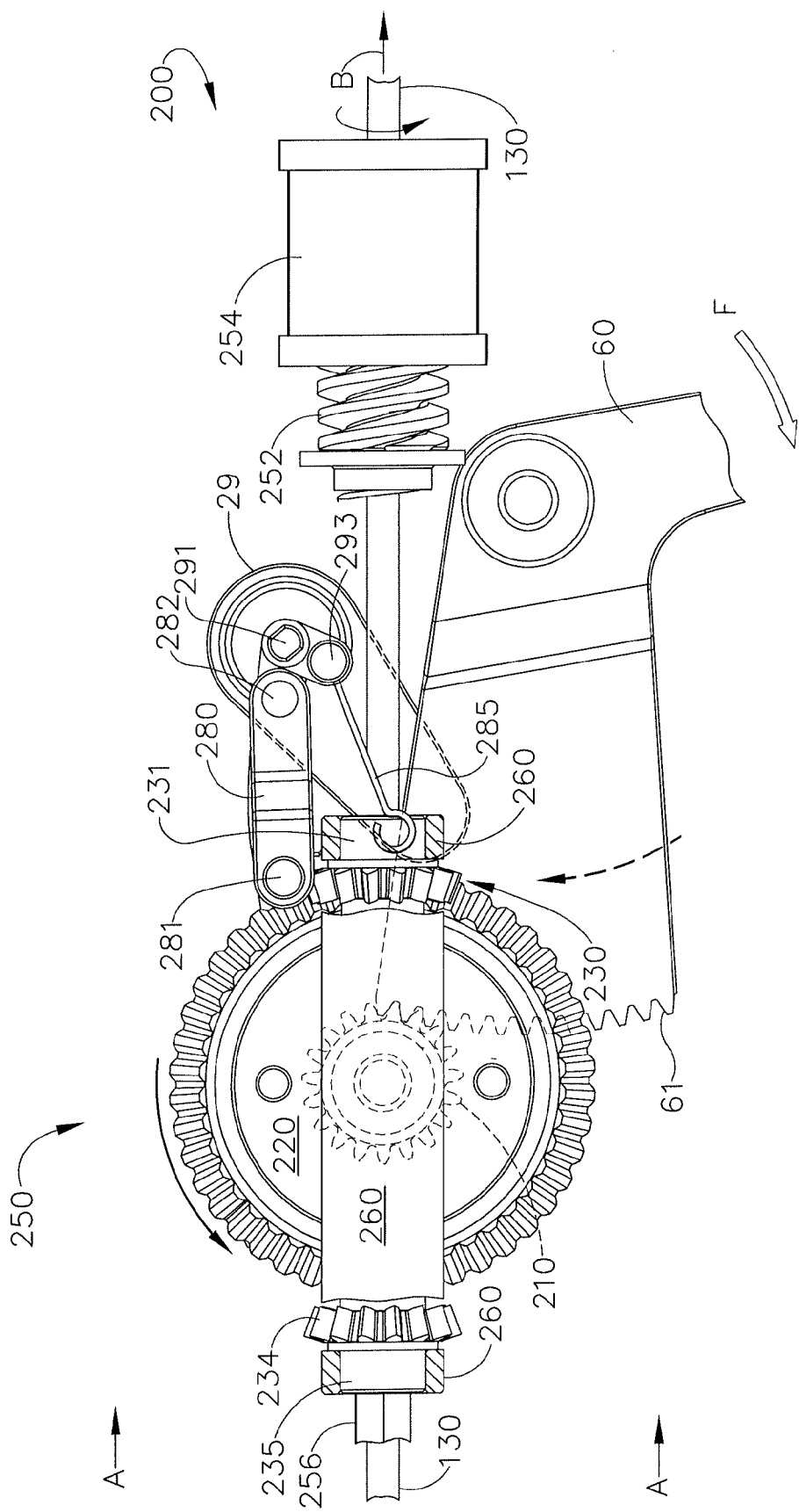
FIG. 9 is a right side view of the drive shift mechanism of FIG. 8, with the drive shift mechanism in an initial position configured to advance the cutter distally.
Figure 10:
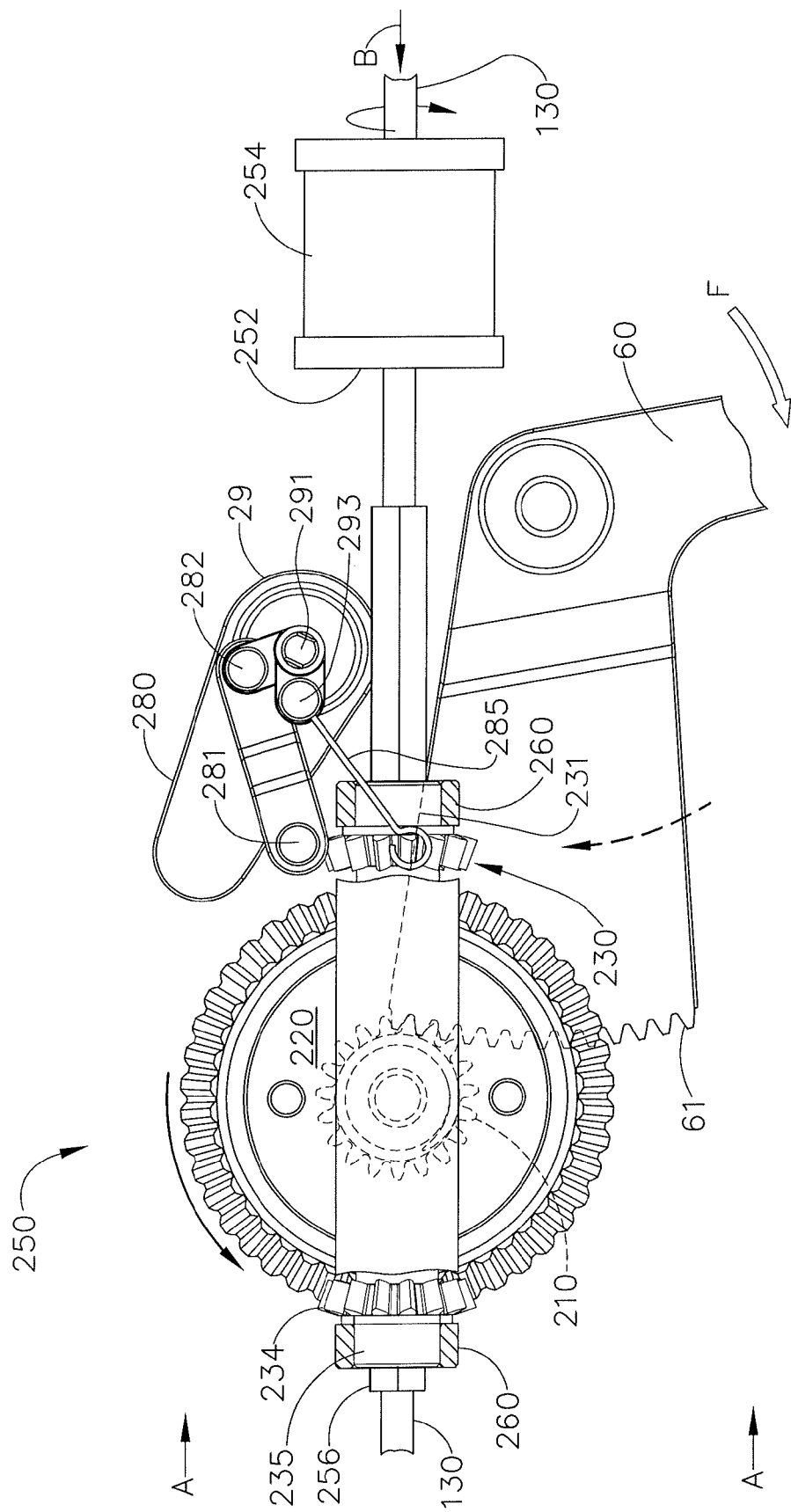
FIG. 10 is a right side view of the drive shift mechanism of FIG. 8, with the drive shift mechanism in position configured to retract the cutter proximally.

As shown in FIGS. 9-10, tissue cutting mechanism (200) of the present example is connected to trigger (28) by engagement of gear teeth (61) with a rotating spur gear (210). Actuation of trigger (28) engages teeth (61) with spur gear (210) to rotate gear (210) around a spur pin (212) that is operatively attached to left handle half (30). As shown in FIG. 4, movement of the trigger (28) from an un-actuated position to an actuated position (see directional arrow located between trigger (28) and pistol grip (27)) results in clockwise rotation of spur gear (210). As trigger (28) is released, the vacuum generated by vacuum pump (310) and/or the resilience of torsion spring (500) assists in returning trigger (28) to the un-actuated position, and spur gear (210) reverses directions and rotates counter-clockwise.

A one-way ratchet (218) is located between spur gear (210) and a large bevel gear (220). Spur gear (210) and bevel gear (220) are separate, and both rotate around spur pin (212). One-way ratchet (218) engages spur gear (210) with bevel gear (220) as trigger (28) is activated, and disengages spur gear (210) from bevel gear (220) when handle (28) is released. In operation, one-way ratchet (218) rotates bevel gear (220) clockwise as the operator pulls trigger (28) closed; and as the operator releases trigger (28), one way ratchet (218) disengages from the counterclockwise rotating spur gear (210), and bevel gear (220) becomes stationary. By way of example only, one-way ratchet (218) can be a simple dog clutch mechanism (not shown) with opposing sawtooth shaped teeth on each gear (210, 220) respectively, with the teeth intermeshing around spur pin (212) to drive in one rotational direction (around spur pin (212)) and to slip in the opposite direction. The teeth of such a dog clutch mechanism can be beveled on one side to spread gears (210, 220) apart to slip when rotated in the opposite rotational direction. A spring (not shown) can be placed around spur pin (212) (e.g., between left cover (30) and spur gear (210)) and used to normally bias spur gear (210) and bevel gear (220) together to drivingly engage the dog clutch mechanism. Other embodiments of a one-way ratchet (218) can include but are not limited to a ratchet and pawl, a sprag clutch, or a one way torsion spring encircling a pin to grip in one rotational direction and to release in the opposite rotational direction. Other suitable ratcheting mechanisms, clutching mechanisms, or other features or configurations, will be apparent to those of ordinary skill in the art in view of the teachings herein. Alternatively, spur gear (210) and bevel gear (220) may be unitary in some versions.

Referring to FIG. 4, hand actuation of trigger (28) rotates spur gear (210) clockwise, engages one way ratchet (218), and rotates bevel gear (220) clockwise. Rotary motion of bevel gear (220) is then transferred to cutter (130) by rotationally engaging a distal bevel gear (230) (FIG. 7) with large bevel gear (220). The rotational direction and translational direction of cutter (130) changes depending on whether proximal bevel gear (230) or distal bevel gear (234) is engaged with large bevel gear (220). A shift mechanism (250) is provided to change rotational direction and translational direction of cutter (130) in response to movement of directional reversal lever (29).

Figure 7:
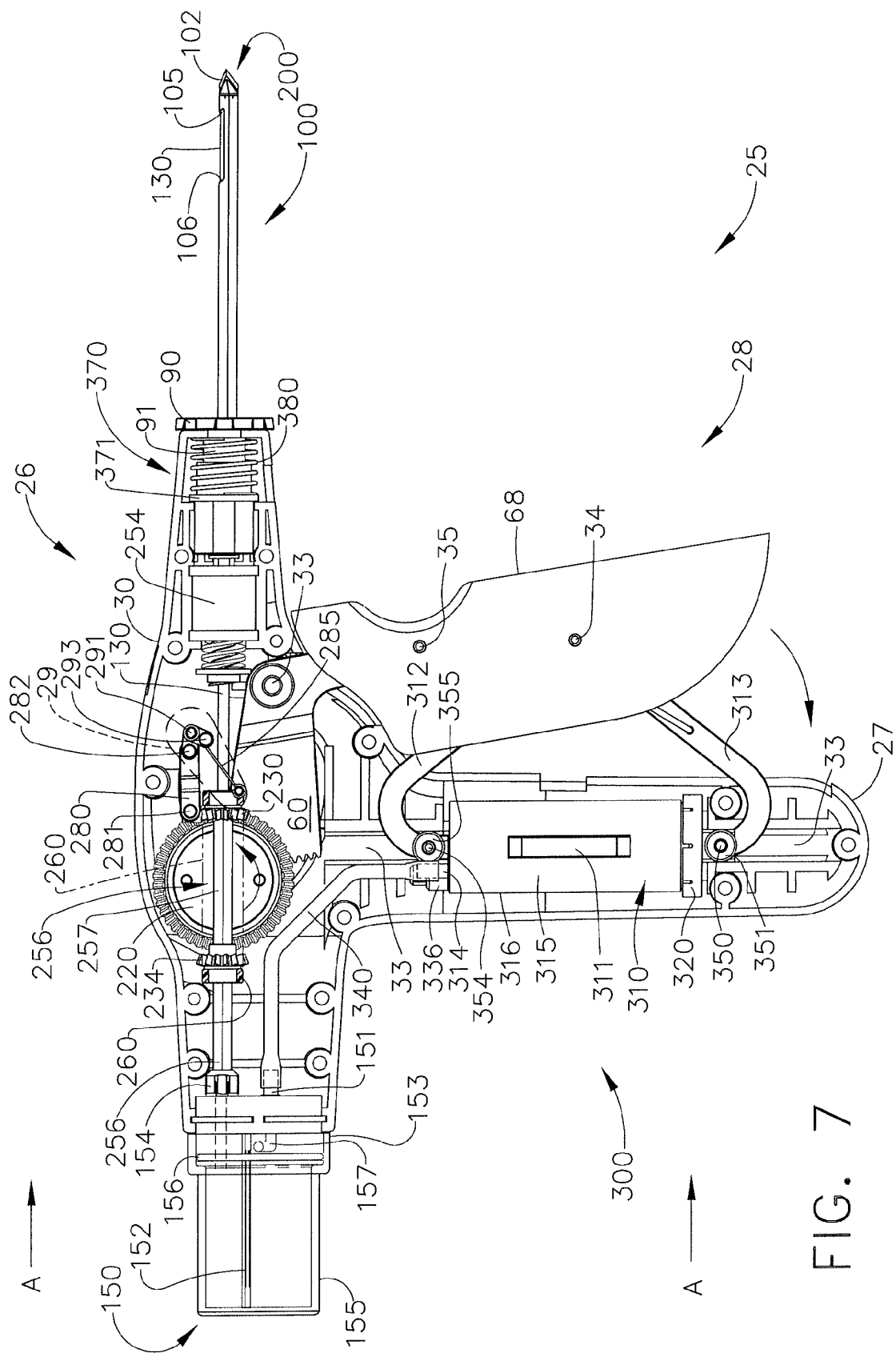
FIG. 7 is a right side view of the biopsy device of FIG. 1 with a right cover removed and the trigger in an un-actuated position.

Referring to FIG. 7, trigger (28) is being actuated by the operator (not shown) and is moving toward pistol grip (27). Spur gear (210) is rotating (on far side of bevel gear (220)), and one-way ratchet (218) engages spur gear (210) with bevel gear (220) such that bevel gear (220) rotates counterclockwise (see arrow on gear (220) in FIG. 7) with spur gear (210). Directional reversal lever (29) is in the first position X (FIGS. 1, 4, 7, 9), which brings distal bevel gear (230) of shift mechanism (250) into rotational and driving contact with bevel gear (220). Rotational movement of distal bevel gear (230) delivers rotational and translational movement to the cutter (130) in response to actuation of trigger (28) by the operator.

1. Exemplary Shift Mechanism

Figure 8:
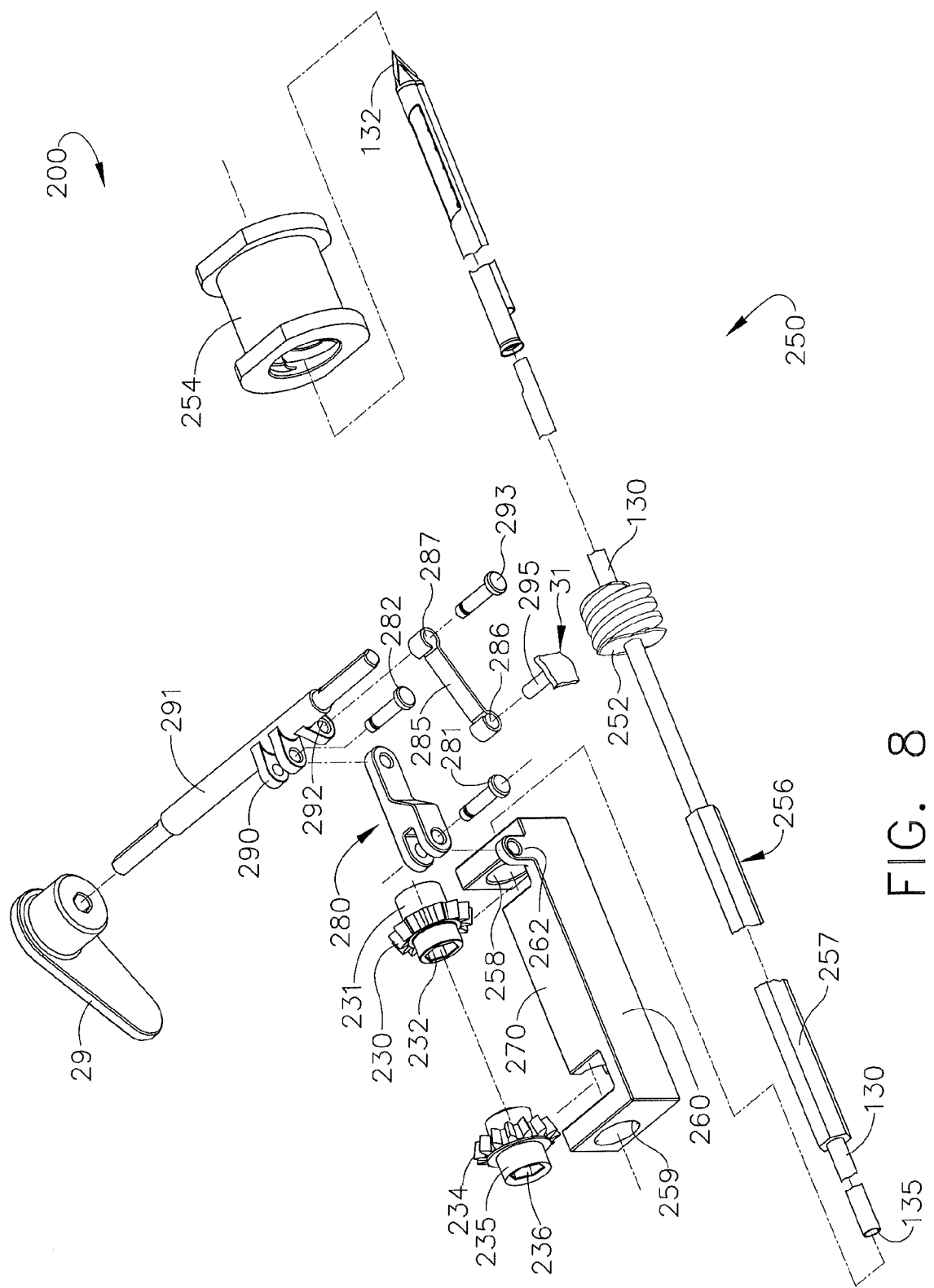
FIG. 8 is an exploded view of the drive shift mechanism of the biopsy device of FIG. 1.

Shift mechanism (250) of the present example is best shown in FIGS. 7-10, and is operable to reverse the rotational and translational movement of cutter (130) in response to a positional change of reversal lever (29). As shown in FIG. 8, shift mechanism (250) includes cutter (130) and an externally threaded screw (252) that is fixedly attached thereto by overmolding, adhesives, or any other method of attachment. Externally threaded screw (252) is configured to threadably engage within an internally threaded stationary nut (254) of shift mechanism (250). Internally threaded stationary nut (254) is cylindrical in shape and is received in and constrained by left and right covers (30, 31). With internally threaded stationary nut (254) captured in left and right covers (30, 31), rotation of cutter (130) rotates externally threaded screw (252) within threaded stationary nut (254), and threaded engagement moves cutter (130) and externally threaded screw (252) longitudinally. Counter-clockwise rotation of hollow cutter (130) moves hollow cutter (130) proximally, away from piercing tip (102), to open tissue aperture (105); and clockwise rotation translates hollow cutter (130) distally, toward piercing tip (102), to close tissue aperture (105). All rotational directions of hollow cutter (130) in this example are taken from the view A-A As shown in FIG. 8, shift mechanism (250) further comprises proximal bevel gear (234), distal bevel gear (230), and a cutter driver (256) fixedly attached to the hollow cutter (130) by a process such as overmolding or adhesion. Cutter driver (256) is spaced proximally from externally threaded screw (252) and further comprises a hexagonal drive portion (257) with a hexagonal cross section. Cutter driver (256) is configured to slidingly mount within a hex bore (232) at a center of distal gear (230) and a proximal hex bore (236) at a center of proximal gear (234). Hexagonal bores (232, 236) are configured to slide on and rotatably engage with hexagonal drive portion (257) of the cutter driver (256). Thus, cutter (130) rotates unitarily with bevel gears (230, 234) in this example, while being permitted to translate longitudinally relative to bevel gears (230, 234).

Distal gear (230) also comprises a distal bearing (231) configured to rotatably mount within a distal opening (258) from the inside of a shift fork (260); and proximal gear (234) has a proximal bearing (235) configured to rotatably mount (from the inside) within a proximal opening (259) within shift fork (260). Both gears (230, 234) are secured longitudinally inside of the "C" shape of shift fork (260) by a spacer (270) sized to fit between mounted gears (230, 234). Spacer (270) is shown as attached to shift fork (260) but can be separate piece that is placed over the cutting needle (30) between gears (230, 234) mounted in shift fork (260). Cutter (130) and cutter driver (256) is inserted through the proximal end of shift fork (260), through distal and proximal hex bores (232, 236) of gears (230, 234), and through the distal end of shift fork (260) to slidingly secure the assembly together within shift fork (260). Longitudinal movement of shift fork (260) (in either direction) moves the assembly of proximal and distal bevel gears (234, 230) and shift fork 260 together along hexagonal drive portion (257) of cutter driver (256).

Shift fork (260) is operably coupled to directional reversal lever (29) by a shift rod (280). A first pin (281) pivotally connects a proximal forked end of shift rod (280) to a tab (262) of shift fork (260); and a second pin (282) pivotally connects a distal end of shift rod (280) to a clevis (290) in a toggle rod (291). Toggle rod (291) attaches to directional reversal lever (29) and rotates in response to movement of directional reversal lever (29). Movement of directional reversal lever (29) rotates toggle rod (291), engages shift rod (280), and moves shift fork (260) longitudinally within handle halves (30, 31) to engage trigger (28) to cutter (130) through either proximal bevel gear (234) or distal bevel gear (230). An over-center leaf spring (285) is pivotally attached at one end (287) to a flange (292) of toggle rod (291) by pin (293). A second end (286) of over-center leaf spring (285) is pivotally attached to a pin (295) in right cover (31). Over-center leaf spring (285) biases (and holds) directional reversal lever (29) (and shift mechanism (250)) at one of either the X position or the Y position.

2. Exemplary Operation of the Shift Mechanism at Position X

The operation of shift mechanism (250) is best shown in FIGS. 9-10, wherein shift mechanism (250) and portions of tissue cutting mechanism (200) are shown with covers (30, 31) and trigger cover (68) removed. In FIG. 9, directional reversal lever (29) is in the first position X, and shift rod (280) has moved shift fork (260) proximally to bring distal bevel gear (230) into operative contact with bevel gear (220). In this view, a force F is being applied to inner member (60) of trigger (28) to rotatingly engage gear teeth (61) with spur gear (210). Ratchet (218) is rotating bevel gear (220) counter-clockwise (see arrow), and the toothed engagement of distal bevel gear (230) with bevel gear (220) is rotating cutter driver (256) and cutter (130) in a clockwise direction as viewed from A-A. Proximal bevel gear (234) and externally threaded screw (252) are also rotating clockwise (with proximal bevel gear (234) essentially "freewheeling"). The clockwise rotation of externally threaded screw (252) in internally threaded nut (254) is translating screw (252), hollow cutter (130), and cutter driver (256) distally to the right as indicated by the arrow B. Gears (234, 230) are rotating and hexagonal cutter driver (256) is rotating and sliding longitudinally therethrough while being driven by distal bevel gear (230). Over-center leaf spring (285) is over center and is holding shift mechanism (250) in restraint at the position shown.

3. Exemplary Operation of the Shift Mechanism at Position Y

In FIG. 10, directional reversal lever (29) has been moved to position Y and shift rod (280) has moved shift fork (260) distally to bring proximal bevel gear (234) into operative contact with large bevel gear (220). In this view, the force F is being applied to inner member (60) of trigger (28) to rotatingly engage gear teeth (61) with spur gear (210), and to rotate bevel gear (220) counter-clockwise (see arrow). The engagement of proximal bevel gear (234) with bevel gear (220) rotates proximal bevel gear (234), which rotates cutter driver (256) and cutter (130) in a counter-clockwise direction as viewed from A-A. Rotating cutter (130) also rotates externally threaded screw (252) and distal bevel gear (230) counter-clockwise (with distal bevel gear (230) essentially "freewheeling"). The counter-clockwise rotation of externally threaded screw (252) in internally threaded nut (254) is translating the hollow cutter (130) and externally threaded screw (252) proximally to the left, as indicated by the arrow B in FIG. 10. Once again, over-center leaf spring (285) is over center and is holding shift mechanism (250) in restraint at the position shown.

It should be understood that tissue cutting mechanism (200) and shift mechanism (250) may be varied in a number of ways. By way of example only, either or both mechanisms (200, 250) may include electromechanical components, including but not limited to motors or solenoids. Either or both mechanisms (200, 250) may also include various alternative mechanical components, features, or methods of operation. Other suitable features, components, configurations, and methods of operation for tissue cutting mechanism (200) and shift mechanism (250) will be apparent to those of ordinary skill in the art in view of the teachings herein.

III. Exemplary Operation of the Biopsy Device

As noted above, biopsy device (25) of the present example is a manually actuated and manually powered device. Manual actuation of trigger (28) simultaneously powers tissue cutting mechanism (200) and vacuum generating mechanism (300) to collect and store tissue samples within tissue collection chamber (150). As described below, one or more actuations of trigger (28) may be required to sever, collect, and store the tissue samples within biopsy device (25).

In one example of operation, biopsy device (25) can be provided to the surgeon or operator with cutter (130) in a distal-most position (e.g., closing off tissue aperture (105)). This position can be easily verified by visually looking at tissue aperture (105). With cutter (130) in a distal-most position, directional reversal lever (29) is moved to position "Y" (see FIG. 1) to configure tissue cutting mechanism (200) to retract cutter (130) proximally and open tissue aperture (105) in response to actuations of trigger (28). If cutter (130) is retracted into the needle portion (100) and tissue aperture (105) is open, the operator moves directional reversal lever (29) to position "X" (see FIG. 1) so that cutter (130) will move distally in response to trigger (28) actuations and advance distally along tissue aperture (105) to cut tissue. For the following description, cutter (130) is in a distal-most position and directional reversal lever (29) is moved to position "Y".

With cutter (130) in a distal-most position and directional reversal lever (29) at position "Y", the surgeon or operator places piercing tip (102) against tissue. Using visualization such as unassisted visualization, x-rays, ultrasound, MRI and the like, the operator inserts needle portion (100) into tissue and positions needle portion (100) adjacent to a suspect lesion or tumor (e.g., within a patient's breast or elsewhere). If desired, needle portion (100) can be rotated with knob (90) to better position or orient tissue aperture (105) adjacent to the tissue lesion. Once tissue aperture (105) is in position, the operator begins manually actuating or pumping trigger (28) to power biopsy device (25) and to acquire the tissue sample.

Referring now to the elements shown in FIGS. 4-6, with directional reversal lever (29) at position "Y", the first actuation of trigger (28) toward pistol grip (27) moves pump (310) of vacuum generating mechanism (300) from the position of FIG. 5 to that of FIG. 6. The movement of pump (310) pulls piston (318) down and cylinder portion (316) up to create or draw a vacuum. The vacuum created by the manual actuation of trigger (28) is communicated through flexible hose (340) to the collection base (153), and to tissue sample container (155) of tissue collection chamber (150). The vacuum is then communicated from tissue collection chamber (150) into cutter lumen (131) of cutter (130). Vacuum from lumen (131) is then communicated to hollow cutter passage (106) and lateral passage (107) within the needle portion (100). With cutter (130) at the distal-most position, auto pressure regulator (370) is biased to a distal-most position, and air passage (372), lateral passage (107), and hollow cutter passage (106) are open to atmospheric pressure air (FIG. 11).

The actuations of trigger (28) also power tissue cutting mechanism (200) at the same time the actuations power vacuum generating mechanism (300). As trigger (28) is depressed, the movement of trigger (28) moves gear teeth (61) in an arc to rotate spur gear (210) around pin (212). In FIG. 4, one-way ratchet (218) drives bevel gear (220) clockwise; and in FIG. 7, one-way ratchet (218) drives bevel gear (220) counter-clockwise. In FIG. 7, as bevel gear (220) rotates counter-clockwise, distal bevel gear (230) is engaged with bevel gear (220) and is rotated clockwise around the longitudinal axis extending within a center of cutter (130). As distal bevel gear (230) rotates, it rotates cutter driver (256), and hence cutter (130), to retract cutter (130) proximally to open tissue aperture (105). In particular, as cutter (130) rotates, externally threaded screw (252) moves cutter (130) and the auto pressure regulator (370) proximally. When auto pressure regulator (370) moves proximally to position air passage (372) proximal to seal (96), the venting or delivery of air at atmospheric pressure (through air passage (372)) is shut off to lateral passage (107) and hollow cutter passage (106). Vacuum is now delivered to lateral passage (107) to draw tissue into tissue aperture (105).

After about three repeated manual actuations of trigger (28), cutter (130) moves to the distal-most position of FIG. 12, and vacuum pump (310) draws tissue into tissue aperture (105). At this point, a visual indicator, an auditory sound, or a hard stop can be provided to indicate the distal-most position of cutter (130) to inform the operator that directional reversal lever (29) needs to be moved to position "X" (see FIG. 1). With directional reversal lever (29) at position "X", the operator continues to pump or actuate and release trigger (28) to both draw vacuum to pull tissue into tissue aperture (105) and to advance and rotate cutter (130) to sever the tissue extending therein.

As cutter (130) approaches the distal-most position of FIG. 11, air passage (372) of auto pressure regulator (370) opens again to vent or deliver air at atmospheric pressure to lateral passage (107) and to hollow cutter passage (106). Cutter (130) may continue to rotate to at least some degree without advancing further when cutter (130) has reached the distal-most position. When cutter (130) has completely severed the tissue sample protruding into tissue aperture (105), the air at atmospheric pressure is conducted into air passage (372) along lateral passage (107), through vacuum passages (108), into cutter passage (106), and into lumen (131) of cutter (130) to create a pressure gradient to push the severed tissue sample therein proximally into tissue sample container (150). The tissue sample is deposited on the tissue collection grid (152), and any fluid communicated through lumen (131) passes through grid (152). It will be appreciated that several tissue samples may be obtained from a patient without having to withdraw needle portion (100) from the patient. In other words, biopsy device (25) may be used to obtain multiple tissue samples with just a single insertion of needle portion (100) into a patient.

It should be understood that there are a variety of other ways in which biopsy device (25) may be operated. Such alternative methods of use may be performed using biopsy device (25) of the present example or using variations of biopsy device (25) of the present example. Various alternative methods of use will be apparent to those of ordinary skill in the art in view of the teachings herein.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, comprising:
(a) a body;
(b) a needle extending distally from the body, wherein the needle comprises:
(i) a cannula defining an internal lumen and a transverse tissue receiving aperture in communication with the internal lumen, wherein the cannula comprises a longitudinally extending tubular sidewall, wherein a distal portion of the sidewall comprises a first portion and a second portion in contact with the first portion, wherein the first portion distally terminates at a first longitudinal position, wherein the second portion distally terminates at a second longitudinal position distal to the first longitudinal position, wherein the first portion is in contact with the second portion at a third longitudinal position that is proximal to the first longitudinal position to thereby substantially seal a distal end of the internal lumen, and
(ii) a tissue piercing tip integral with the cannula, wherein the tissue piercing tip and the cannula together comprise a homogenous continuum of material; and
(c) a cutter movable relative to the needle, wherein the cutter includes an edge configured to sever tissue protruding through the transverse tissue receiving aperture.

2. The biopsy device of claim 1, wherein the cutter is disposed in the internal lumen of the cannula.

3. The biopsy device of claim 2, wherein the internal lumen of the cannula is defined by an inner surface of the cannula, wherein the cutter has an outer surface, wherein a space between the outer surface of the cutter and the inner surface of the cannula defines a gap, wherein the gap is sized to permit communication of atmospheric air through the space between the outer surface of the cutter and the inner surface of the cannula.

4. The biopsy device of claim 3, further comprising a pressure regulator configured to selectively seal or vent the gap relative to atmospheric air.

5. The biopsy device of claim 1, wherein the cutter is longitudinally translatable relative to the needle.

6. The biopsy device of claim 1, wherein the cutter is rotatable relative to the needle.

7. The biopsy device of claim 1, wherein the cutter is tubular and the edge configured to sever tissue is annular and extends about the full circumference of the cutter.

8. The biopsy device of claim 1, wherein the tissue piercing tip comprises a pair of sharp edges converging at a sharp point.

9. The biopsy device of claim 1, wherein the transverse tissue receiving aperture is formed through the sidewall of the cannula proximal to the distal portion.

10. The biopsy device of claim 1, wherein the second portion forms the tissue piercing tip.

11. The biopsy device of claim 1, further comprising a vacuum pump positioned in the body.

12. The biopsy device of claim 11, wherein the vacuum pump is manually operable to induce a vacuum.

13. The biopsy device of claim 1, wherein the body comprises a pistol grip and an actuator trigger, wherein the actuator trigger is movable toward the pistol grip to move the cutter relative to the needle.

14. The biopsy device of claim 1, further comprising a tissue sample holder coupled with the body, wherein the tissue sample holder is configured to receive tissue samples severed by the cutter.

15. The biopsy device of claim 14, wherein the cutter is configured to communicate tissue samples proximally through the cutter to reach the tissue sample holder.

16. A biopsy device, comprising:
   (a) a body;
   (b) a needle extending distally from the body, wherein the needle comprises:
      (i) a cannula comprising a tubular sidewall having a distal end and a proximal end, wherein the tubular sidewall defines a transverse tissue receiving aperture proximal to the distal end, wherein the tubular sidewall further defines an inner lumen in communication with the transverse tissue receiving aperture, wherein the distal end comprises a first portion of the sidewall in contact with a second portion of the sidewall at a region of contact, wherein the cannula defines a longitudinal axis, and
      (ii) a tissue piercing tip comprising a flat blade member, wherein the tissue piercing tip extends distal to the region of contact, wherein the flat blade member is formed by the second portion of the sidewall, such that the tissue piercing tip is a unitary feature of the cannula, wherein the second portion of the sidewall is bent inwardly such that the flat blade member defines a plane extending along the longitudinal axis of the cannula; and
   (c) a cutter movable relative to the needle to sever tissue protruding through the transverse tissue receiving aperture.

\* \* \* \* \*